United States Patent
Mees et al.

(10) Patent No.: US 6,897,180 B2
(45) Date of Patent: May 24, 2005

(54) STABILIZATION OF ACID CATALYSTS

(75) Inventors: Filip Mees, Grobbendonk (BE);
Etienne Vansant, Zoersel (BE); Marcel Johannes Janssen, Kessel-Lo (BE);
Luc R. M. Martens, Meise (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/295,994

(22) Filed: Nov. 15, 2002

(65) Prior Publication Data
US 2003/0149321 A1 Aug. 7, 2003

(30) Foreign Application Priority Data
Jan. 3, 2002 (EP) .............................. 02250030

(51) Int. Cl.$^7$ .............................................. B01J 29/06
(52) U.S. Cl. ..................................... 502/214; 502/208
(58) Field of Search ................................. 502/208, 214

(56) References Cited

U.S. PATENT DOCUMENTS

| | | | |
|---|---|---|---|
| 4,681,864 A | 7/1987 | Edwards et al. ............... 502/63 |
| 4,861,938 A | 8/1989 | Lewis et al. ................. 585/640 |
| 4,874,590 A | * 10/1989 | Staniulis et al. .......... 423/239.1 |
| 5,013,699 A | 5/1991 | Vassilakis et al. ............ 502/73 |
| 5,185,310 A | 2/1993 | Degnan et al. ............. 502/214 |
| 5,248,647 A | 9/1993 | Barger ......................... 502/214 |
| 5,250,484 A | * 10/1993 | Beck et al. .................... 502/71 |
| 6,051,745 A | 4/2000 | Wu et al. ..................... 585/638 |
| 6,051,746 A | 4/2000 | Sun et al. ..................... 585/639 |
| 2003/0004056 A1 | * 1/2003 | Mees et al. .................. 502/208 |

FOREIGN PATENT DOCUMENTS

| | | | |
|---|---|---|---|
| EP | 0 203 005 | 2/1989 | ........... G09F/13/22 |
| JP | 7-155614 | 6/1995 | ............ B01J/29/85 |
| WO | WO 00/74846 | 12/2000 | ............ B01J/20/04 |
| WO | WO 00/74848 | 12/2000 | ............ B01J/29/85 |
| WO | WO 00/75072 | 12/2000 | ............ C01B/37/00 |
| WO | WO 01/25150 | 12/2000 | ............ B01J/29/00 |

OTHER PUBLICATIONS

Hawley's Condensed Chemical Dictionary, 13th Edition, 1997, p. 244.*
Briend et al., *J. Phys. Chem.* vol. 99, pp. 8270–8276 (1999).

* cited by examiner

Primary Examiner—Christina Johnson

(57) ABSTRACT

The invention is directed to a method of stabilizing metalloaluminophosphate molecular sieves and catalysts derived therefrom. In particular, the invention is directed to a method of treating such molecular sieves with chemisorbed ammonia, which may be easily desorbed before or during use and after storage. The invention is also directed to formulating the molecular sieve into a catalyst useful in a process for producing olefin(s), preferably ethylene and/or propylene, from a feedstock, preferably an oxygenate containing feedstock.

64 Claims, 6 Drawing Sheets

őSTABILIZATION OF ACID CATALYSTS

FIELD OF INVENTION

This invention relates to a method of stabilizing metalloaluminophosphate molecular sieves during storage and handling, to stabilized metalloaluminophosphate molecular sieves and metalloaluminophosphate molecular sieve containing catalysts and to their use in adsorption and conversion processes, especially the conversion of oxygenates to olefins.

BACKGROUND OF THE INVENTION

Olefins are traditionally produced from petroleum feedstock by catalytic or steam cracking processes. These cracking processes, especially steam cracking, produce light olefin(s) such as ethylene and/or propylene from a variety of hydrocarbon feedstock. It has been known for some time that oxygenates, especially alcohols, are convertible into light olefin(s). Methanol, the preferred alcohol for light olefin production, is typically synthesized from the catalytic reaction of hydrogen, carbon monoxide and/or carbon dioxide in a methanol reactor in the presence of a heterogeneous catalyst. The preferred methanol conversion process is generally referred to as a methanol-to-olefin(s) process, where methanol is converted to primarily ethylene and/or propylene in the presence of a molecular sieve.

Some of the most useful molecular sieves for converting methanol to olefin(s) are the metalloaluminophosphates such as the aluminophosphates (ALPO') and the silicoaluminophosphates (SAPO'). SAPO synthesis is described in U.S. Pat. No. 4,440,871, which is herein fully incorporated by reference. SAPO is generally synthesized by the hydrothermal crystallization of a reaction mixture of silicon-, aluminium- and phosphorus-sources and at least one templating agent. Synthesis of a SAPO molecular sieve, its formulation into a SAPO catalyst, and its use in converting a hydrocarbon feedstock into olefin(s), particularly where the feedstock is methanol, is shown in U.S. Pat. Nos. 4,499,327, 4,677,242, 4,677,243, 4,873,390, 5,095,163, 5,714,662 and 6,166,282, all of which are herein fully incorporated by reference.

It has been discovered that metalloaluminophosphate molecular sieves such as aluminophosphate (ALPO) and especially silicoaluminophosphate (SAPO) molecular sieves, are relatively unstable to moisture containing atmospheres such as ambient air when in the calcined or partially calcined state; this state is sometimes referred to as the activated state. It has also been observed that the relative stability is in part related to the nature of the organic templating agent used in the manufacture of the SAPO molecular sieve. Briend et al., J.Phys. Chem. 1995, 99, 8270–8276, teaches that SAPO-34 loses its crystallinity when the template has been removed from the sieve and the de-templated, activated sieve has been exposed to air. Data is presented, however, which suggest that over at least the short term, crystallinity loss is reversible. Even over a period of a couple years, the data suggest that crystallinity loss is reversible when certain templates are used.

U.S. Pat. No. 4,681,864 to Edwards et al. discusses the use of SAPO-37 molecular sieve as a commercial cracking catalyst. It is disclosed that activated SAPO-37 molecular sieve has poor stability. However, stability can be improved by using a particular activation process. According to the process, retained organic template present from the synthesis of the SAPO-37 is removed from the core structure of the sieve just prior to contacting with feed to be cracked. The process calls for subjecting the sieve to a temperature of 400–800° C. within the catalytic cracking unit.

U.S. Pat. No. 5,185,310 to Degnan et al. discloses another method of activating silicoaluminophosphate molecular sieve compositions. The method calls for contacting a crystalline silicoaluminophosphate with gel alumina and water, and thereafter heating the mixture to at least 425° C. The heating process is first carried out in the presence of an oxygen-depleted gas, and then in the presence of an oxidizing gas. The objective of the heating process is to enhance the acid activity of the catalyst. The acid activity is enhanced as a result of the intimate contact between the alumina and the molecular sieve.

U.S. Pat. No. 6,051,746 to Sun et. al. discloses a process for the conversion of oxygenated organic materials to olefins using a modified small pore molecular sieve catalyst. The molecular sieve catalyst is modified with polynuclear aromatic heterocyclic compounds in which at least three interconnected ring structures are present having at least one nitrogen atom as a ring substituent, and with each ring having at least five ring members.

European Published Application EP-A2-0,203,005 discusses the use of SAPO-37 molecular sieve in a zeolite catalyst composite as a commercial cracking catalyst. According to the document, if organic template is retained in the SAPO-37 molecular sieve until a catalyst composite containing zeolite and the SAPO-37 molecular sieve is activated during use, and if thereafter the catalyst is maintained under conditions wherein exposure to moisture is minimized, the crystalline structure of the SAPO-37 zeolite composite remains stable.

PCT Publication No. WO 00/74848 to Janssen et al. describes a method of protecting the catalytic activity of silicoaluminophosphate molecular sieves by covering the catalytic sites with a shield prior to contacting with an oxygenate feedstock. The shielding may be achieved by retaining template within the pores of the molecular sieve, by using carbonaceous materials, or by using an anhydrous gas or liquid environment.

PCT Publication No. WO 00/75072 to Fung et. al. discloses a method for addressing the problems relating to protecting molecular sieves from damage due to contact with moisture and damage due to physical contact. The method requires the heat treatment of a molecular sieve containing a template under conditions effective to remove a portion of the template from the microporous structure and cooling the heated molecular sieve to leave an amount of template or degradation product thereof effective to cover catalytic sites within the microporous structure.

PCT Publication No. WO 00/74846 to Janssen et. al. discloses a method for preserving the catalytic activity of silicoaluminophosphate molecular sieves which comprises heating of template-containing silicoaluminophosphate in an oxygen depleted environment under conditions effective to provide an integrated catalyst life which is greater than that obtained using a non-oxygen depleted environment.

U.S. Pat. No. 6,051,745 to Wu et. al. is concerned with overcoming the problem of the excessive production of coke, which occurs when some silicoaluminophosphates are used as catalysts in the conversion of oxygenated hydrocarbons to olefins. The solution proposed is the use of nitrided silicoaluminophosphates. Nitridation is achieved by the reaction of the silicoaluminophosphate with ammonia at elevated temperatures, typically in excess of 700° C. The nitridation reaction is essentially irreversible and destroys irreversibly the acidic sites of the molecular sieve, as the acidic OH groups are converted to $NH_2$ groups during the nitridation process.

U.S. Pat. No. 4,861,938 to Lewis et.al describes a process for converting feedstocks. Matrix material used in the manufacture of the catalyst for the process may be conditioned prior to catalyst manufacture by exposure to ammonia.

U.S. Pat. No. 5,248,647 to Barger describes a process for the hydrothermal treatment of silicoaluminophosphate molecular sieves. The process requires the treatment to be undertaken at temperatures in excess of 700° C. to destroy a large proportion of the acid sites whilst at the same time retaining a significant proportion of the original crystallinity. Also disclosed in this document is a test method for determining the molecular sieve acidity. This test method requires the adsorption of ammonia onto the molecular sieve, followed by desorption within the temperature range of 300 to 600° C. and titration of the desorbed ammonia As seen from the disclosures described herein, many metalloaluminophosphate molecular sieves will exhibit a shortened catalytic life when exposed to a moisture-containing environment. This loss of catalytic life is, in some instances, irreversible, and can occur over a very short period of time. In essence, this loss of catalytic life is due to a loss in the number of acid catalytic sites. In addition there may be irreversible loss of molecular sieve crystallinity and porosity on ageing during storage and handling after manufacture.

It is desirable therefore to develop methods for the treatment of metalloaluminophosphate molecular sieves and catalysts containing these molecular sieves, which ensure that the catalytic properties and physical properties of these materials, such as porosity and crystallinity, are retained after storage and handling.

SUMMARY OF THE INVENTION

The present invention provides a method for the preparation of stabilized metalloaluminophosphate molecular sieves and metalloaluminophosphate molecular sieve containing catalysts, and to their use in adsorption and conversion processes, especially the conversion of oxygenates to olefins, particularly light olefin(s). In the context of the present invention reference will be made throughout this specification to metalloaluminophosphate molecular sieves; this term as used in this specification encompasses aluminophosphate (ALPO) and silicoaluminophosphate (SAPO) molecular sieves and derivatives of these molecular sieves as hereinbefore and hereinafter described.

In one embodiment the invention is directed to a method of providing a stabilized metalloaluminophosphate molecular sieve, which method comprises the steps of a. providing a metalloaluminophosphate molecular sieve having a framework structure, b. treating the metalloaluminophosphate molecular sieve with a source of ammonia under conditions to chemisorb ammonia with the metalloaluminophosphate molecular sieve, and c. maintaining the ammonia chemisorbed with the metalloaluminophosphate molecular sieve for a period of at least 24 hours.

In another embodiment the invention is directed to a method of providing an active metalloaluminophosphate molecular sieve, which method comprises the steps of a. providing a metalloaluminophosphate molecular sieve having a framework structure, b. treating the metalloaluminophosphate molecular sieve with a source of ammonia under conditions to chemisorb ammonia with the metalloaluminophosphate molecular sieve, c. maintaining the ammonia chemisorbed with the metalloaluminophosphate molecular sieve for a period of at least 24 hours, and d. desorbing the chemisorbed ammonia.

In another embodiment the present invention provides a method for the manufacture of a catalyst composition, which method comprises the steps of a. forming a mixture comprising at least one metalloaluminophosphate molecular sieve having a framework structure with at least one binder material and/or at least another catalytically active material, and b. treating the mixture with a source of ammonia under conditions to chemisorb ammonia with the metalloaluminophosphate molecular sieve.

In yet a further embodiment the present invention provides a method for the manufacture of a catalyst composition, which method comprises, forming a mixture comprising at least one metalloaluminophosphate molecular sieve having ammonia chemisorbed thereon with at least one binder material and/or at least another catalytically active material, to form a catalyst composition.

In a further embodiment the present invention provides a stabilized metalloaluminophosphate molecular sieve, which comprises at least one aged metalloaluminophosphate molecular sieve and chemisorbed ammonia.

In yet a further embodiment the present invention provides a molecular sieve composition comprising at least one metalloaluminophosphate molecular sieve in admixture with at least one binder and/or at least another catalytically active material and chemisorbed ammonia.

In an additional embodiment the present invention provides a molecular sieve composition comprising at least one metalloaluminophosphate molecular sieve having ammonia chemisorbed thereon and in admixture with at least one binder and/or at least another catalytically active material.

The present invention also provides for the use of ammonia to stabilize a metalloaluminophosphate molecular sieve during storage and/or handling.

In a further embodiment the present invention provides a method for storing metalloaluminophosphate molecular sieves which method comprises maintaining the metalloaluminophosphate molecular sieve in contact with ammonia in a chemisorbed state during storage.

The metalloaluminophosphate molecular sieves and compositions comprising these molecular sieves as made by or described in the above embodiments and in the detailed description of the present invention find utility in absorption processes and in hydrocarbon conversion processes.

Accordingly the present invention also provides for a hydrocarbon conversion process comprising the steps of:

a) introducing a feedstock to a reactor system in the presence of a metalloaluminophosphate molecular sieve as prepared or described in any one of the embodiments of the present invention;

b) withdrawing from the reactor system an effluent stream; and c) passing the effluent gas through a recovery system recovering at least one or more conversion products.

In this embodiment, the invention is preferably directed to a process for producing olefin(s) or alkyl amines in the presence of any of the metalloaluminophosphate molecular sieves and catalyst compositions of the present invention.

BRIEF DESCRIPTION OF THE DRAWINGS

The present invention will be better understood by reference to the Detailed Description of the Invention when taken together with the attached drawings wherein.

DETAILED DESCRIPTION OF THE INVENTION

Introduction

Figure 1:
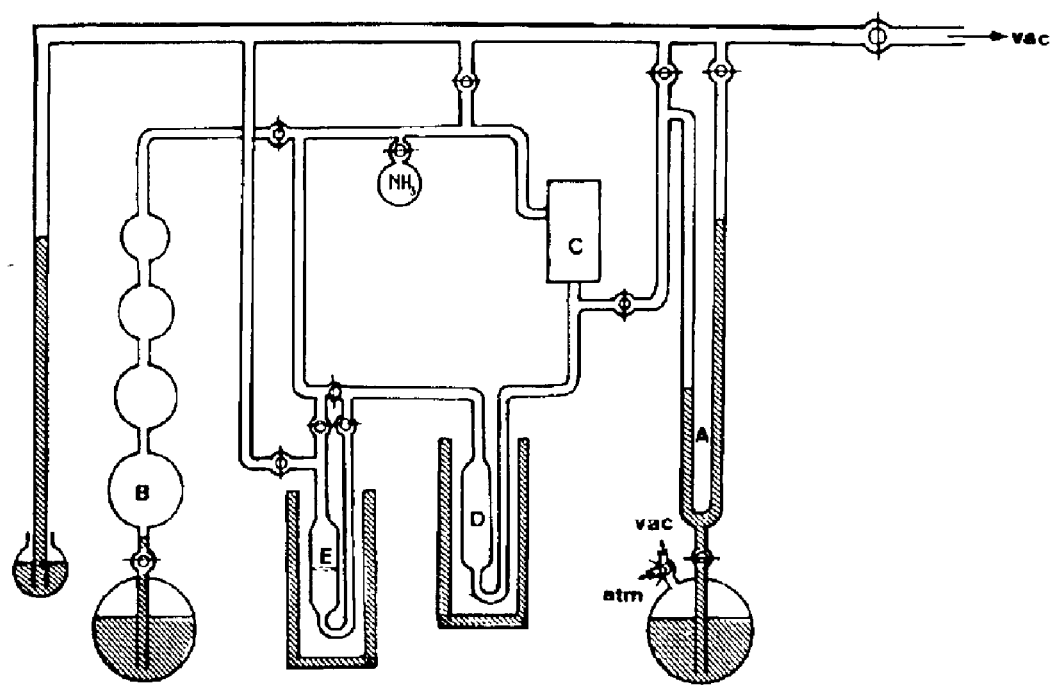
FIG. 1 shows a dynamic gas-volumetric adsorption apparatus suitable for treatment of metalloaluminophosphate molecular sieves with ammonia.

The invention is primarily directed toward a method of stabilizing metalloaluminophosphate molecular sieves. It has been found that the treatment of metalloaluminophosphate molecular sieves with ammonia so that the ammonia is chemisorbed results in stabilized metalloaluminophosphates that are resistant to degradation during exposure to moisture. Through this method, treated metalloaluminophosphate molecular sieve materials and catalyst compositions are provided which retain most if not all of their original adsorption, catalytic and/or physical properties on storage even after extensive periods of exposure to ambient atmosphere or steam. Without being bound to any particular theory, it is believed that the ammonia reacts in a reversible way with the Broensted acid sites within the metalloaluminophosphate molecular sieve and in doing so protects them from attack by moisture during storage and handling.

Chemisorption of Ammonia

A key aspect of the present invention is the chemisorption of ammonia with acid catalytic cites of the metalloaluminophosphate molecular sieve. As indicated above it is known in the art to treat such molecular sieves with ammonia under nitridation conditions. Nitridation results in an irreversible chemical reaction between acid sites of the molecular sieve and ammonia or other nitrogen sources. The nitridation reaction is essentially irreversible and destroys irreversibly the acidic sites of the molecular sieve, as the acidic OH groups are converted to $NH_2$ groups during the nitridation process. This is in contrast with the process of chemisorption according to the present invention, which is a chemical adsorption process in which a weak chemical bond is formed between molecules in the gaseous or liquid state and a solid surface. Due to this weak bonding the process is reversible upon the application of heat. In the context of the present invention ammonia is the molecule, which is in either the gaseous or liquid state, and the solid surface is the metalloaluminophosphate molecular sieve.

Chemisorption Process

Preferably prior to chemisorption of the ammonia the metalloaluminophosphate molecular sieve is activated. The primary function of the activation process is to remove volatile compounds and template utilized in the synthesis of the molecular sieve that may still be present in or on the molecular sieve. It is envisaged that in the process of the present invention the molecular sieve may be partially activated. By partially activated is meant that a proportion of the template or by-products of the template is not removed prior to chemisorption. It is preferred that substantially all the template be removed. Activation is achieved using conventional calcination techniques and conditions as discussed below. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

The activated molecular sieve may be chemisorbed with ammonia under a variety of conditions. These conditions are selected to ensure that ammonia is chemisorbed with at least the Broensted acid sites of the molecular sieve. The ammonia is chemisorbed in the liquid or gaseous state. Preferably it is chemisorbed in the gaseous state. In one embodiment the activated molecular sieve is introduced into a treatment vessel, which enables the molecular sieve to be degassed. This is typically achieved by utilizing a vacuum, preferably with the application of heat. Typically the molecular sieve may be degassed under vacuum at a temperature within the range of 10 to 600° C., and preferably 20 to 300° C. In an alternative embodiment the molecular sieve is treated as activated without degassing.

The ammonia may be introduced to the treatment vessel containing the degassed molecular sieve or the as activated molecular sieve. The ammonia may be introduced with or without the use of an inert carrier gas such as dry nitrogen or similar gas. When used in a gaseous mixture the partial pressure of ammonia in the mixture is not critical. Preferably, the ammonia is present in excess of that required to react with at least the Broensted acid sites within the molecular sieve. The ammonia may be introduced at ambient temperatures or at elevated temperatures. It is important that the temperature is selected so that the ammonia does not react with the molecular sieve under nitridation conditions. It is possible to determine suitable temperatures for any given molecular sieve by observing the chemisorption and desorption of ammonia using analytical techniques such as the Infrared techniques described herein. If a temperature is used that results in an irreversible reaction with the ammonia as may be determined by these techniques, then a lower reaction temperature should be selected. The ammonia may be reacted with the molecular sieve at a temperature of less than 500° C., ideally less than 450° C., preferably less than 300° C.; ideally within the temperature range of 0 to 500° C. or 10 to 450° C., preferably 20 to 300° C., or 20 to 450° C., and most preferably 100 to 250° C. It has been found to be particularly effective if the chemisorption reaction is undertaken at temperatures preferably in excess of 100° C., more preferably in excess of 150° C., and most preferably in excess of 200° C. The ammonia may initially be introduced at a low temperature e.g. less than 100° C. and the temperature may then be raised above this temperature during the reaction. The exact time required to complete the chemisorption process is dependent on the amount of acidity present in the molecular sieve. The amount of acidity may be determined by test methods known in the art such as ammonia TPD. The time for chemisorption and/or the amount of ammonia used and/or the temperature of chemisorption may be used to ensure that sufficient ammonia is chemisorbed. It is also possible to determine the optimum conditions for any given molecular sieve by undertaking a series of adsorption and desorption experiments to determine under what conditions complete chemisorption is achieved. Once determined these conditions may be used in the chemisorption process. In this regard the ammonia TPD test method and Infrared spectroscopy may be used. Typically, when gaseous ammonia is used and the chemisorption is undertaken on a degassed sample of molecular sieve, the chemisorption process is complete after 30 minutes exposure to ammonia at a temperature in excess of 100° C. At temperatures in excess of 100° C. it is the Broensted acid sites, which are substantially, chemisorbed with the ammonia; at temperatures below 100° C. other sites including Broensted acid sites and non-Broensted acid sites may be chemisorbed with the ammonia.

It is envisaged that the chemisorption process with ammonia may be undertaken on a composition comprising metalloaluminophosphate molecular sieve and in particular a catalyst composition. In this embodiment the composition comprising metalloaluminophosphate molecular sieve and other materials e.g. catalyst components, is exposed to ammonia under conditions that result in the chemisorption of ammonia with the molecular sieve. This exposure to ammonia may be achieved by introducing the ammonia into the end zone of the calcination unit used in the manufacture of a catalyst composition. This zone is typically at temperatures below the calcination temperature as the catalyst is being cooled before being introduced into storage drums. In this and other embodiments the ammonia may be introduced in the presence of an inert gas such as nitrogen.

The molecular sieve comprising chemisorbed ammonia is stable when stored under ambient conditions. The molecular sieve is also stable in the presence of water vapour at temperatures of up to 300° C., preferably of up to 250° C., more preferably of up to 200° C. By stable is meant that there is less reduction in the catalytic activity of the chemisorbed molecular sieve compared to the non-chemisorbed molecular sieve when stored under or exposed to the same conditions. The molecular sieve comprising chemisorbed ammonia may be maintained in the chemisorbed state for an extended period of time, which is typically at least 24 hours and which may be for any period of storage or handling greater than 24 hours. In one embodiment the molecular sieve is maintained in the chemisorbed state for at least 36 hours, preferably at least 48 hours and most preferably at least 72 hours. Ideally it is held in this state as long as possible before use. In one embodiment the molecular sieve is held in the chemisorbed state until it is utilized in the manufacture of a catalyst composition. In a further embodiment it is held in the chemisorbed state prior to introduction as the catalyst or part of a catalyst composition into a catalyzed reaction. In this embodiment the preferred catalyzed reaction is a methanol-to-olefins process.

It is also envisaged within the scope of the present invention that the chemisorption process may be undertaken on used metalloaluminophosphate molecular sieve or used catalyst compositions comprising metalloaluminophosphate molecular sieve. During conversion processes, such as methanol-to-olefin processes, it may be necessary to shut the reactor down in either an emergency or in a planned shutdown and maintenance cycle. When this occurs it is often necessary to remove the used catalyst from the reactor and to place it into temporary storage, which is usually under an inert atmosphere. Sometimes removal is not necessary or desirable and the catalyst is maintained within the plant itself. In both situations the catalyst is under risk of losing its catalytic activity and/or other properties due to ageing effects. In addition during shut down and start-up the reactor may be under conditions, which generate significant quantities of steam at high temperature i.e. superheated steam, which is particularly harmful to metalloaluminophosphate molecular sieve containing catalysts. The ammonia chemisorption method of the present invention has been found to be particularly effective in protecting metalloaluminophosphate molecular sieve materials against the effects of steam as would be present in the methanol-to-olefins process. In this embodiment the used catalyst may be treated by ammonia chemisorption as the catalyst is removed from the methanol-to-olefins plant; the ammonia being desorbed when the ammonia chemisorbed catalyst can be re-introduced to the plant. In an alternative embodiment the used catalyst is treated within the plant during or after shutdown. In a particularly preferred embodiment the used catalyst is exposed to ammonia within the plant at temperatures above those at which steam significantly degrades the metalloaluminophosphate molecular sieve. In a methanol-to-olefins process significant steam damage may occur within the temperature range of 100 to 350° C. Higher temperatures should be avoided as under these conditions in the reactor the undesirable nitridation reaction may occur.

Desorption Conditions

The metalloaluminophosphate molecular sieve in the ammonia chemisorbed state may be regenerated by desorption of the ammonia. This may be achieved by heating the ammonia chemisorbed metalloaluminophosphate molecular sieve at temperatures in excess of 200° C., and preferably in excess of 400° C., and most preferably in excess of 600° C. This desorption may be achieved using a muffle furnace or similar furnace. It may also be achieved by using the same equipment used for calcination during manufacture of the molecular sieve or catalyst compositions contacting the molecular sieve. In one embodiment the ammonia may be removed during the manufacture of a formulated catalyst under spray drying conditions. In a further embodiment the ammonia may be removed in situ on introduction of the ammonia chemisorbed metalloaluminophosphate molecular sieve to a catalytic conversion process such as a methanol-to-olefins process. This may be achieved by introduction of ammonia chemisorbed metalloaluminophosphate molecular sieve to the regeneration unit of the plant.

Aged Molecular Sieve

In the context of the present invention an aged metalloaluminophosphate molecular sieve is a metalloaluminophosphate molecular sieve as synthesized or formulated as a catalyst, which has been stored for an extended period of time after synthesis. By extended periods of time is meant a period of greater than 24 hours, preferably greater than 36 hours, more preferably greater than 48 hours, and most preferably greater than 72 hours. In another embodiment, an aged metalloaluminophosphate molecular sieve is a metalloaluminophosphate molecular sieve that has been used in a catalytic process and has been removed from that process or temporarily retained under non-optimum process conditions such as in a shutdown phase. The period of ageing may be under ambient conditions or elevated temperature, it may be undertaken under an inert atmosphere or a vacuum, for example in a sealed container such as storage drum or metalloaluminophosphate molecular sieve holding facility after manufacture of the sieve or a catalyst composition containing the metalloaluminophosphate molecular sieve. In the context of the present invention aged metalloaluminophosphates are typically present in large amounts i.e. the bulk state. By bulk state is meant in the form of a large batch of material or catalyst comprising the metalloaluminophosphate. Typically a bulk sample has a batch size of greater than 1 kilogram, preferably greater than 10 kilogram and most preferably greater than 50 kilogram. The ageing may be undertaken in the presence of an inert gas in addition to the chemisorbed ammonia. In the present invention it is possible to utilize grades of inert gases which were hitherto unacceptable for metalloaluminophosphate molecular sieve storage due to inter alia their moisture content. Such gases may be of lower purity and quality e.g. they may contain higher than normal levels of impurities such as oxygen and/or moisture.

Metalloaluminophosphate Acidity and Infrared

Metalloaluminophosphate molecular sieve materials such as silicoaluminophosphate molecular sieves comprise a three-dimensional microporous crystal framework structure and exhibit a particularly desirable Broensted acid OH group spectrum in the Infrared, when the template material has been properly removed. Broensted acid OH groups can be conveniently characterized by Diffused Reflectance Infrared (DRIFTS) spectroscopy. The groups can be found throughout a range of 4000 cm$^{-1}$ to 3400 cm$^{-1}$ of the IR spectrum. However, silicoaluminophosphate molecular sieves which exhibit desirable catalytic activity upon appropriate template removal have Broensted acid OH groups having one or more bands in the IR with wave numbers ranging from about 3630 cm$^{-1}$ to about 3580 cm$^{-1}$, with non-Broensted OH groups like Al—OH, P—OH and/or Si—OH being largely located in the range of about 4000 cm$^{-1}$ to about 3630 cm$^{-1}$. The non-Broensted OH groups are also typically located on the external surface of the molecular sieve or at regions within the sieve that exhibit internal defects.

In order to preserve catalytic activity, i.e., maintain acid catalyst sites, this invention provides a method, which comprises chemisorbing ammonia with the Broensted acid sites. The chemisorption may be observed and monitored through the use of DRIFTS. When the ammonia is chemisorbed the infrared absorption bands relating to the Broensted acid sites decrease in intensity and are replaced by a new series of a infrared absorption bands at lower wave numbers between 2300 cm$^{-1}$ and 3500 cm$^{-1}$, when ammonia is fully chemisorbed. When the chemisorbed ammonia is subsequently removed through desorption these characteristic infrared absorptions decrease in intensity and eventually disappear whilst the original Broensted acid absorption bands re-appear at higher wave numbers. The intensity of the restored Broensted acidity infrared bands is comparable to the bands observed prior to ammonia chemisorption. This infrared behaviour is typical with the process of the present invention and is a good method for determining that the acid sites and especially the Broensted acid sites of the molecular sieve have been protected through chemisorption of ammonia and restored through desorption of the ammonia.

Extended exposure of metalloaluminophosphate molecular sieves to ambient atmosphere results in a loss of catalytic activity. One suitable method for determining this activity and its loss is to determine the methanol adsorption capacity (MAC) of the molecular sieve after synthesis and activation and to monitor this capacity with time after a period of storage. Ideally the MAC should remain as high as possible up to the point at which the molecular sieve is used in a conversion process such as a methanol-to-olefins process. For molecular sieve catalysts which are activated in situ, i.e. the template is removed on introduction of the molecular sieve to the conversion process, the time between activation and actual contact with feed is short enough such that the initial methanol adsorption capacity is essentially equivalent to the methanol adsorption capacity at feed contact. During conventional storage conditions e.g. under an inert atmosphere, this is not normally achieved as the catalyst is progressively degraded by attack from moisture. In the present invention the chemisorbed ammonia is effective in retaining the methanol uptake properties of the molecular sieve, which are higher than those, achieved without ammonia chemisorption. The measurement of MAC may be used in the context of the present invention to demonstrate the effective stabilization due to the chemisorption of ammonia. The use of ammonia chemisorption results in improved MAC values after storage. According to this invention, it is preferred that the MAC after ammonia desorption is at least 15% of the original MAC prior to chemisorption of ammonia, preferably at least 40%, more preferably at least 60%, and most preferably at least 80%. Techniques for measuring methanol adsorption capacity are known to those of ordinary skill in the art.

Molecular Sieves and Catalysts Thereof

The metalloaluminophosphate molecular sieves which may be used in the present invention have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AIPO$_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. No. 4,759,919, and U.S. Pat. No. 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO$_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other metalloaluminophosphate molecular sieves include those described in EP-0 888 187 B 1 (microporous crystalline metallophosphates, SAPO$_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), PCT WO 01/64340 published Sep. 7, 2001 (thorium containing molecular sieve), and R. Szostak, *Handbook of Molecular Sieves*, Van Nostrand Reinhold, New York, N.Y. (1992), which are all herein fully incorporated by reference.

The most preferred molecular sieves are SAPO molecular sieves, and metal substituted SAPO molecular sieves. In one embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof.

The metalloaluminophosphate molecular sieve may be represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanide'of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

As used herein, the term mixture is synonymous with combination and is considered a composition of matter having two or more components in varying proportions, regardless of their physical state. In particular, it encompasses physical mixtures as well as intergrowths of at least two different molecular sieve structures; such as for example those described in PCT Publication No. WO 98/15496 and co-pending U.S. Ser. No. 09/924,016 filed Aug. 7, 2001. In an embodiment, the molecular sieve is an intergrowth material having two or more distinct phases of crystalline structures within one molecular sieve composition. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type. In a further embodiment the molecular sieve comprises a mixture of intergrown material and non-intergrown material.

The method of stabilization of the present invention may be utilized with metalloaluminophosphate molecular sieves which are particularly unstable to moisture exposure e.g. morpholine templated SAPO-34 and may also be used to stabilize relatively moisture insensitive molecular sieves such as dual templated (DPA and TEAOH) SAPO-34 materials which may be significantly affected during extended periods of ageing or on exposure to steam.

Molecular Sieve Synthesis

Generally, metalloaluminophosphate molecular sieves are synthesized by the hydrothermal crystallization of one or more of a source of aluminium, a source of phosphorous, a source of silicon, a templating agent, and a metal containing compound. Typically, a combination of sources of silicon, aluminium and phosphorous, optionally with one or more templating agents and/or one or more metal containing compounds are placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting.

In a typical synthesis of the molecular sieve, the phosphorous-, aluminium-, and/or silicon-containing components are mixed, preferably while stirring and/or agitation and/or seeding with a crystalline material, optionally with an alkali metal, in a solvent such as water, and one or more templating agents, to form a synthesis mixture that is then heated under crystallization conditions of pressure and temperature as described in U.S. Pat. Nos. 4,440,871, 4,861,743, 5,096,684, and 5,126,308, which are all herein fully incorporated by reference.

The preferred templating agent or template is a tetraethylammonium compound, such as tetraethyl ammonium hydroxide (TEAOH), tetraethyl ammonium phosphate, tetraethyl ammonium fluoride, tetraethyl ammonium bromide, tetraethyl ammonium chloride and tetraethyl ammonium acetate. The most preferred templating agent is tetraethyl ammonium hydroxide and salts thereof, particularly when producing a silicoaluminophosphate molecular sieve. In one embodiment, a combination of two or more of any of the above templating agents is used in combination with one or more of a silicon-, aluminium-, and phosphorous-source.

Other suitable metalloaluminophosphate molecular sieves for use in the present invention may be prepared as described in U.S. Pat. No. 5,879,655 (controlling the ratio of the templating agent to phosphorous), U.S. Pat. No. 6,005,155 (use of a modifier without a salt), U.S. Pat. No. 5,475,182 (acid extraction), U.S. Pat. No. 5,962,762 (treatment with transition metal), U.S. Pat. No. 5,925,586 and U.S. Pat. No. 6,153,552 (phosphorous modified), U.S. Pat. No. 5,925,800 (monolith supported), U.S. Pat. No. 5,932,512 (fluorine treated), U.S. Pat. No. 6,046,373 (electromagnetic wave treated or modified) U.S. Pat. No. 6,051,746 (polynuclear aromatic modifier), U.S. Pat. No. 6,225,254 (heating template), PCT WO 01/36329 published May 25, 2001 (surfactant synthesis), PCT WO 01/25151 published Apr. 12, 2001 (staged acid addition), PCT WO 01/60746 published Aug. 23, 2001 (silicon oil), U.S. patent application Ser. No. 09/929,949 filed Aug. 15, 2001 (cooling molecular sieve), U.S. patent application Ser. No. 09/615,526 filed Jul. 13, 2000 (metal impregnation including copper), U.S. patent application Ser. No. 09/672,469 filed Sep. 28, 2000 (conductive microfilter), and U.S. patent application Ser. No. 09/754,812 filed Jan. 4, 2001(freeze drying the molecular sieve), which are all herein fully incorporated by reference.

In one preferred embodiment, when a templating agent is used in the synthesis of a molecular sieve, it is preferred that the templating agent is substantially, preferably completely, removed after crystallization by numerous well known techniques, for example, heat treatments such as calcination. Calcination involves contacting the molecular sieve containing the templating agent with a gas, preferably containing oxygen, at any desired concentration at an elevated temperature sufficient to either partially or completely decompose and oxidize the templating agent.

In one embodiment, the molecular sieve has a Si/Al ratio less than 0.65, preferably less than 0.40, more preferably less than 0.32, and most preferably less than 0.20.

Method for Making Molecular Sieve Catalyst Compositions

Once the molecular sieve is synthesized the molecular sieve may then be treated to chemisorb ammonia and then formulated into a molecular sieve catalyst composition. Alternatively the metalloaluminophosphate molecular sieve as synthesized with or without activation may be formulated into a catalyst composition prior to ammonia chemisorption. In either instance the metalloaluminophosphate molecular sieve may be combined with a binder and/or a matrix material to form a molecular sieve catalyst composition or a formulated molecular sieve catalyst composition. This formulated molecular sieve catalyst composition is formed into useful shape and sized particles by well-known techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminium chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminium oxide matrix following heat treatment.

Aluminium chlorhydrol, a hydroxylated aluminium based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminium oxyhydroxide, γ-alumina, boehmite, diaspore, and transitional aluminas such as α-alumina, β-alumina, γ-alumina, δ-alumina, ε-alumina, κ-alumina, and ρ-alumina, aluminium trihydroxide, such as gibbsite, bayerite, nordstrandite, doyelite, and mixtures thereof.

In another embodiment, the binders are alumina sols, predominantly comprising aluminium oxide, optionally including some silicon. In yet another embodiment, the binders are peptised alumina made by treating alumina hydrates such as pseudobohemite, with an acid, preferably an acid that does not contain a halogen, to prepare sols or aluminium ion solutions. Non-limiting examples of commercially available colloidal alumina sols include Nalco 8676 available from Nalco Chemical Co., Naperville, Ill., and Nyacol available from The PQ Corporation, Valley Forge, Pa.

The metalloaluminophosphate molecular sieve with or without chemisorbed ammonia, may be combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry; it has a low fresh surface area, and it packs together easily due to its platelet structure. A preferred average particle size of the matrix material, most preferably kaolin, is from about 0.1 $\mu$m to about 0.6 $\mu$m with a D90 particle size distribution of less than about 1 $\mu$m.

In one embodiment, the binder, the molecular sieve with or without chemisorbed ammonia and the matrix material are combined in the presence of a liquid to form a molecular sieve catalyst composition, where the amount of binder is from about 2% by weight to about 30% by weight, preferably from about 5% by weight to about 20% by weight, and more preferably from about 7% by weight to about 15% by weight, based on the total weight of the binder, the molecular sieve and matrix material, excluding the liquid (after calcination).

In another embodiment, the weight ratio of the binder to the matrix material used in the formation of the molecular sieve catalystcomposition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

Upon combining the molecular sieve with or without chemisorbed ammonia, and the matrix material, optionally with a binder, in a liquid to form a slurry, mixing, preferably rigorous mixing is needed to produce a substantially homogeneous mixture containing the molecular sieve. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution. In the present invention the use of a metalloaluminophosphate molecular sieve, which comprises chemisorbed ammonia, is beneficial in the catalyst formulation process as the chemisorbed ammonia protects the molecular sieve from the detrimental effects of the water utilized in the formulation process.

The molecular sieve with and without chemisorbed ammonia and matrix material, and the optional binder, may be in the same or different liquid, and may be combined in any order, together, simultaneously, sequentially, or a combination thereof. In the preferred embodiment, the same liquid, preferably water is used. The molecular sieve, matrix material, and optional binder, are combined in a liquid as solids, substantially dry or in a dried form, or as slurries, together or separately. If solids are added together as dry or substantially dried solids, it is preferable to add a limited and/or controlled amount of liquid.

In one embodiment, the slurry of the molecular sieve with or without chemisorbed ammonia, binder and matrix materials is mixed or milled to achieve a sufficiently uniform slurry of sub-particles of the molecular sieve catalyst composition that is then fed to a forming unit that produces the molecular sieve catalyst composition. In a preferred embodiment, the forming unit is spray dryer. Typically, the forming unit is maintained at a temperature sufficient to remove most of the liquid from the slurry, and from the resulting molecular sieve catalyst composition. The resulting catalyst composition when formed in this way takes the form of microspheres. If chemisorbed ammonia is present prior to spray drying it may if desired be removed during the spray drying process by selecting appropriate temperatures to ensure that the ammonia is desorbed. Alternatively the spray drying conditions may be selected to ensure that the chemisorbed ammonia is substantially retained within the spray-dried material.

When a spray drier is used as the forming unit, typically, the slurry of the molecular sieve and matrix material, and optionally a binder, is co-fed to the spray drying volume with a drying gas with an average inlet temperature ranging from 200° C. to 550° C., and a combined outlet temperature ranging from 100° C. to about 225° C. In an embodiment, the average diameter of the spray dried formed catalyst composition is from about 40 μm to about 300 μm, preferably from about 50 μm to about 250 μm, more preferably from about 50 μm to about 200 μm, and most preferably from about 65 μm to about 90 μm. If desired the average inlet and/or outlet temperature of the spray drier may be selected to enable the desorption of chemisorbed ammonia to occur during the spray drying process.

During spray drying, the slurry is passed through a nozzle distributing the slurry into small droplets, resembling an aerosol spray into a drying chamber. Atomization is achieved by forcing the slurry through a single nozzle or multiple nozzles with a pressure drop in the range of from 100 psia to 1000 psia (690 kPaa to 6895 kPaa). In another embodiment, the slurry is co-fed through a single nozzle or multiple nozzles along with an atomisation fluid such as air, steam, flue gas, or any other suitable gas.

In yet another embodiment, the slurry described above is directed to the perimeter of a spinning wheel that distributes the slurry into small droplets, the size of which is controlled by many factors including slurry viscosity, surface tension, flow rate, pressure, and temperature of the slurry, the shape and dimension of the nozzle(s), or the spinning rate of the wheel. These droplets are then dried in a co-current or counter-current flow of air passing through a spray drier to form a substantially dried or dried molecular sieve catalyst composition, more specifically a molecular sieve in powder form.

Generally, the size of the powder is controlled to some extent by the solids content of the slurry. However, control of the size of the catalyst composition and its spherical characteristics are controllable by varying the slurry feed properties and conditions of atomisation.

Other methods for forming a molecular sieve catalyst composition is described in U.S. patent application Ser. No. 09/617,714 filed Jul. 17, 2000 (spray drying using a recycled molecular sieve catalyst composition), which is herein incorporated by reference.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapour. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof. During this calcination process chemisorbed ammonia if present may be removed by desorption from the metalloaluminophosphate.

In one embodiment, calcination of the formulated molecular sieve catalyst composition is carried out in any number of well known devices including rotary calciners, fluid bed calciners, batch ovens, and the like. Calcination time is typically dependent on the degree of hardening of the molecular sieve catalyst composition and the temperature.

In a preferred embodiment, the molecular sieve catalyst composition is heated in nitrogen at a temperature of from about 600° C. to about 700C. Heating is carried out for a period of time typically from 30 minutes to 15 hours, preferably from 1 hour to about 10 hours, more preferably from about 1 hour to about 5 hours, and most preferably from about 2 hours to about 4 hours.

Other methods for activating a molecular sieve catalyst composition are described in, for example, U.S. Pat. No. 5,185,310 (heating molecular sieve of gel alumina and water to 450° C.), PCT WO 00/75072 published Dec. 14, 2000 (heating to leave an amount of template), and U.S. application Ser. No. 09/558,774 filed Apr. 26, 2000 (rejuvenation of molecular sieve), which are all herein fully incorporated by reference In addition to the metalloaluminophosphate molecular sieve, the catalyst compositions of the present invention may comprise one or several other catalytically active materials. The present invention encompasses treating with ammonia catalyst compositions comprising one or several metalloaluminophosphate molecular sieve and another catalytically active material. In one embodiment, one or several metalloaluminophosphate molecular sieves are combined with one more of the following non-limiting examples of catalytically active molecular sieves described in the following: Beta (U.S. Pat. No. 3,308,069), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632, 811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527)MCM-14 (U.S. Pat. No. 4,619,818), MCM-22 (U.S. Pat. No. 4,954,325), MCM-41 (U.S. Pat. No. 5,098,684), M-41 S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), titanium aluminosilicates (TASO), TASO-45 (EP-A-0 229,-295), boron silicates (U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345).

In another embodiment, the metalloaluminophosphate may be bound to another molecular sieve, as disclosed for example in the following: SAPO-34 bound ALPO-5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference. Binder may no longer be necessary in such systems.

In a further embodiment, the metalloaluminophosphate molecular sieve may be combined with a metal catalyst, for example as a Fischer-Tropsch catalyst.

Process for Using the Molecular Sieve Catalyst Compositions

The molecular sieve catalysts and compositions of the present invention with chemisorbed ammonia or after desorption of chemisorbed ammonia are useful in a variety of processes including: cracking, hydrocracking, isomerization, polymerisation, reforming, hydrogenation, dehydrogenation, dewaxing, hydrodewaxing, absorption, alkylation, transalkylation, dealkylation, hydrodecylization, disproportionation, oligomerization, dehydrocyclization and combinations thereof.

The preferred processes of the present invention include a process directed to the conversion of a feedstock comprising one or more oxygenates to one or more olefin(s) and a process directed to the conversion of ammonia and one or more oxygenates to alkyl amines and in particular methylamines.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The most preferred process is generally referred to as gas-to-olefins (GTO) or alternatively, methanol-to-olefins (MTO). In a MTO process, typically an oxygenated feedstock, most preferably a methanol containing feedstock, is converted in the presence of a molecular sieve catalyst composition into one or more olefin(s), preferably and predominantly, ethylene and/or propylene, often referred to as light olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapour form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidised bed process (includes a turbulent bed process), preferably a continuous fluidised bed process, and most preferably a continuous high velocity fluidised bed process.

The reaction processes can take place in a variety of catalytic reactors such as hybrid reactors that have a dense bed or fixed bed reaction zones and/or fast fluidised bed reaction zones coupled together, circulating fluidised bed reactors, riser reactors, and the like. Suitable conventional reactor types are described in for example U.S. Pat. Nos. 4,076,796, 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S.

Pat. No. 6,166,282 (fast-fluidised bed reactor), and U.S. patent application Ser. No. 09/564,613 filed May 4, 2000 (multiple riser reactor), which are all herein fully incorporated by reference.

In the preferred embodiment, a fluidised bed process or high velocity fluidised bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of fresh feedstock fed separately or jointly with a vapour feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapour feedstocks are preferably the same composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel; typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidised state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$; preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidise the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See for example U.S. Pat. No. 5,952,538, which is herein fully incorporated by reference.

In another embodiment of the processes for converting an oxygenate such as methanol to one or more olefin(s) using a molecular sieve catalyst composition, the WHSV is from 0.01 $hr^{-1}$ to about 100 $hr^{-1}$, at a temperature of from about 350° C. to 550° C., and silica to $Me_2O_3$ (Me is a Group IIIA or VIII element from the Periodic Table of Elements) molar ratio of from 300 to 2500. See for example EP-0 642 485 B1, which is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time.

Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172 kPaa) to about 150 psia (1034 kpaa), and most preferably from about 30 psia (207 kpaa) to about 60 psia (414 kpaa).

The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference.

In an embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system.

In one embodiment, the cooler regenerated molecular sieve catalyst composition is returned to the regenerator in a continuous cycle, alternatively, (see U.S. patent application Ser. No. 09/587,766 filed Jun. 6, 2000) a portion of the cooled regenerated molecular sieve catalyst composition is returned to the regenerator vessel in a continuous cycle, and another portion of the cooled molecular sieve regenerated molecular sieve catalyst composition is returned to the riser reactor(s), directly or indirectly, or a portion of the regenerated molecular sieve catalyst composition or cooled regenerated molecular sieve catalyst composition is contacted with by-products within the gaseous effluent (PCT WO 00/49106 published Aug. 24, 2000), which are all herein fully incorporated by reference. In another embodiment, a regenerated molecular sieve catalyst composition contacted with an alcohol, preferably ethanol, 1-propnaol, 1-butanol or mixture thereof, is introduced to the reactor system, as described in U.S. patent application Ser. No. 09/785,122 filed Feb. 16, 2001, which is herein fully incorporated by reference.

Other methods for operating a regeneration system are in disclosed U.S. Pat. No. 6,290,916 (controlling moisture), which is herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, preferably after passing through a catalyst cooler. In one embodiment, a carrier, such as an inert gas, feedstock vapour, steam or the like, semi-continuously or continuously, facilitates the introduction of the regenerated molecular sieve catalyst composition to the reactor system, preferably to the one or more riser reactor(s).

By controlling the flow of the regenerated molecular sieve catalyst composition or cooled regenerated molecular sieve catalyst composition from the regeneration system to the reactor system, the optimum level of coke on the molecular sieve catalyst composition entering the reactor is maintained. There are many techniques for controlling the flow of a molecular sieve catalyst composition described in Michael Louge, *Experimental Techniques, Circulating Fluidised Beds*, Grace, Avidan and Knowlton, eds. Blackie, 1997 (336–337), which is herein incorporated by reference.

Coke levels on the molecular sieve catalyst composition are measured by withdrawing from the conversion process the molecular sieve catalyst composition at a point in the process and determining its carbon content. Typical levels of coke on the molecular sieve catalyst composition, after regeneration is in the range of from 0.01 weight percent to about 15 weight percent, preferably from about 0.1 weight percent to about 10 weight percent, more preferably from about 0.2 weight percent to about 5 weight percent, and most preferably from about 0.3 weight percent to about 2 weight percent based on the total weight of the molecular sieve and not the total weight of the molecular sieve catalyst composition.

In one preferred embodiment, the mixture of fresh molecular sieve catalyst composition and regenerated molecular sieve catalyst composition and/or cooled regenerated molecular sieve catalyst composition contains in the range of from about 1 to 50 weight percent, preferably from about 2 to 30 weight percent, more preferably from about 2 to about 20 weight percent, and most preferably from about 2 to about 10 coke or carbonaceous deposit based on the total weight of the mixture of molecular sieve catalyst compositions. See for example U.S. Pat. No. 6,023,005, which is herein fully incorporated by reference.

The gaseous effluent is withdrawn from the disengaging system and is passed through a recovery system. There are many well-known recovery systems, techniques and sequences that are useful in separating olefin(s) and purifying olefin(s) from the gaseous effluent. Recovery systems generally comprise one or more or a combination of a various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like.

The metalloaluminophosphate molecular sieve materials and catalyst compositions of the present invention may be used in the manufacture of alkylamines, using ammonia. Examples of suitable processes are as described in published European Patent Application EP 0 993 867 A1, and in U.S. Pat. No. 6,153,798 to Hidaka et.al, which are herein fully incorporated by reference.

In order to provide a better understanding of the present invention including representative advantages thereof, the following examples are offered.

EXAMPLES

Methods

Dynamic Gas-Volumetric Adsorption Apparatus

The apparatus used for treatment with ammonia was a dynamic gas-volumetric adsorption apparatus as illustrated in FIG. 1.

Briefly, the apparatus consists of two calibrated volumes, the 'dead volume' and the 'ample container'. The dead volume consists of a Hg-manometer (A), a fixed-step gas burette (B), a circulation pump (C) and a cold trap (D). The dead volume is separated from the sample container (E) by two valves and by shutting the interconnecting valve it is possible to enforce a unidirectional flow through the sample container. Both volumes are connected to a high vacuum system (rotation pump+diffusion pump), which allows a pressure reduction to <<0.1 Pa. The apparatus is constructed to maintain this vacuum for several days. Calcined SAPO-34 samples were degassed in sample container (E) overnight in vacuum at 300° C. and then $NH_3$ was contacted in situ with the SAPO-34 at different temperatures. The chemisorption was completed when it was determined through observation of the pressure drop on the Hg-manometer that the pressure has reached a steady value. This occurred after approximately 30 mins using elevated temperatures. When the sample was treated at 20° C. it was necessary due to the volume limitations on the adsorption apparatus to undertake multiple injections and exposures to the ammonia gas; under these conditions chemisorption was completed when a pressure increase was observed indicating that no further ammonia could be chemisorbed onto the sample.

TGA-DTG

TGA measurements were recorded on a Mettler TG 50/TA 3000 thermobalance, controlled by a TClOA microprocessor. The TGA diagrams were recorded under a nitrogen flow (200 mL/min) at a heating rate of 5° C./min.

XRD

X-ray Diffractograms were recorded on a Philips PW 1840 powder diffractometer, using Ni-filtered Cu Kα radiation (X=0.154nm).

$N_2$-Adsorption and Desorption

Porosity and surface area studies were performed on a Quantachrome Autosorb-1-MP automated gas adsorption system. All samples were out gassed for 16 h at 200° C. prior to adsorption. Gas adsorption occurred using nitrogen as the adsorbate at liquid nitrogen temperature (77° K). Micropore volumes were determined using the t-plot method of De Boer, in which the amount of $N_2$ adsorbed is replotted against t. This parameter stands for the multilayer thickness for the adsorption of $N_2$ on a non-porous reference solid.

Methanol Adsorption Capacity

The methanol adsorption capacity is measured in a gravimetric adsorption apparatus, which comprised a quartz spring. After degassing the SAPO-34 in vacuum at 200° C., the sample was cooled to room temperature and methanol vapour was allowed into the system at room temperature. By measuring the weight changes at regular time intervals, not only the adsorption capacity but also the adsorption kinetics was measured. The methanol adsorption capacity (MAC) is the amount of methanol adsorbed when the system is in equilibrium and is given as the increase in weight (in %) of a dehydrated SAPO-34 after methanol uptake.

Methanol Conversion During MTO

The MTO reaction (Methanol-to-Olefins) was performed in a stainless steel, fixed bed continuous reactor. 100% methanol is added as feed. The reaction is carried out at 450° C., a reactor pressure of 15 psig and a WHSV of 26 g/g.hr. Reaction products were analyzed with an on-line GC. Methanol conversion is calculated as 100-(wt. % methanol +wt. % DME) left in the product.

Infrared Spectroscopy

DRIFTS (Diffuse Reflectance Infrared Fourier Transformed Spectroscopy) spectra were recorded on a Nicolet Nexus FTIR spectrometer equipped with an in situ DRIFTS cell (Spectra Tech) and an MCT detector. The SAPO-34 was mixed with KBr (95% KBr; 5% SAPO-34), the measurements were performed in vacuum at 200° C. or 4000C. after degassing the SAPO-34 in situ for 15 minutes. The spectral resolution was 4 $cm^{-1}$. Pure KBr was run as a reference.

Example 1

Preparation of SAPO-34

SAPO-34 was crystallized in the presence of morpholine (R) as templating agent. A mixture of the following mole ratio composition was prepared:

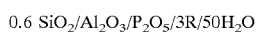

0.6 $SiO_2/Al_2O_3/P_2O_5/3R/50H_2O$ 80.1 g of Condea Pural SB was mixed with 422.0 g of deionised water, to form a slurry. To this slurry was added 135.6 g of phosphoric acid (85%). These additions were made with stirring to form a homogeneous mixture. To this homogeneous mixture 53.2 g of Ludox AS40 was added, followed by the addition of 157.2 g of morpholine (R) with mixing to form a homogeneous mixture. To this homogeneous mixture was added 1.97 g of a seeding slurry containing 8.68 wt % zeolite chabasite crystals.

This homogeneous mixture was crystallized without agitation in a 1 liter stainless steel autoclave. The mixture was heated to 175° C. in 6 hours and kept at this temperature for 48 hours. This provided a slurry of crystalline molecular sieve. The slurry was evenly divided over 2 one liter bottles and the crystals were separated from the mother liquor by centrifuging. The solids in each bottle were further washed 4 times with 850 ml of deionised water. The conductivity of the last wash water was ~40 µS/cm. The solids were dried overnight at 120° C. 15.2% crystals by weight of the initial synthesis mixture were obtained.

Example 2

Treatment and Ageing of SAPO-34 with $NH_3$

Anhydrous ammonia (grade 3.6) was supplied as a liquefied gas from Praxair, Potassium nitrate, p.a. was supplied from Acros organics.

The SAPO-34 was activated (calcined) prior to the modification. Calcination was performed muffle furnace at 625° C. for 4 hours under ambient air (heating rate: 5° C./min). The calcined SAPO-34 was transferred into a dynamic gas-volumetric adsorption apparatus and degassed overnight in vacuum at 300° C. $NH_3$ was contacted in situ with the SAPO-34 for 30 mins at different temperatures leading to different ammonia loadings. The degree of modification was measured volumetrically.

Ageing of the SAPO-34

The SAPO-34 with and without ammonia chemisorption was hydrated (aged) in a moisture-containing atmosphere (90% relative humidity) for periods of time from less than 1 day up to 100 days. 90% relative humidity was established by a saturated $KNO_3$ solution in an exciccator.

Dehydration and Ammonia Desorption of Aged SAPO-34

After the ageing, the SAPO-34 samples were dehydrated in a muffle furnace at 625° C. for 4 hours under ambient air (heating rate: 5° C./min) and at the same time any chemisorbed ammonia if present was desorbed, the samples were then characterized and tested.

Test Results

Methanol Adsorption Capacity

Figure 2:
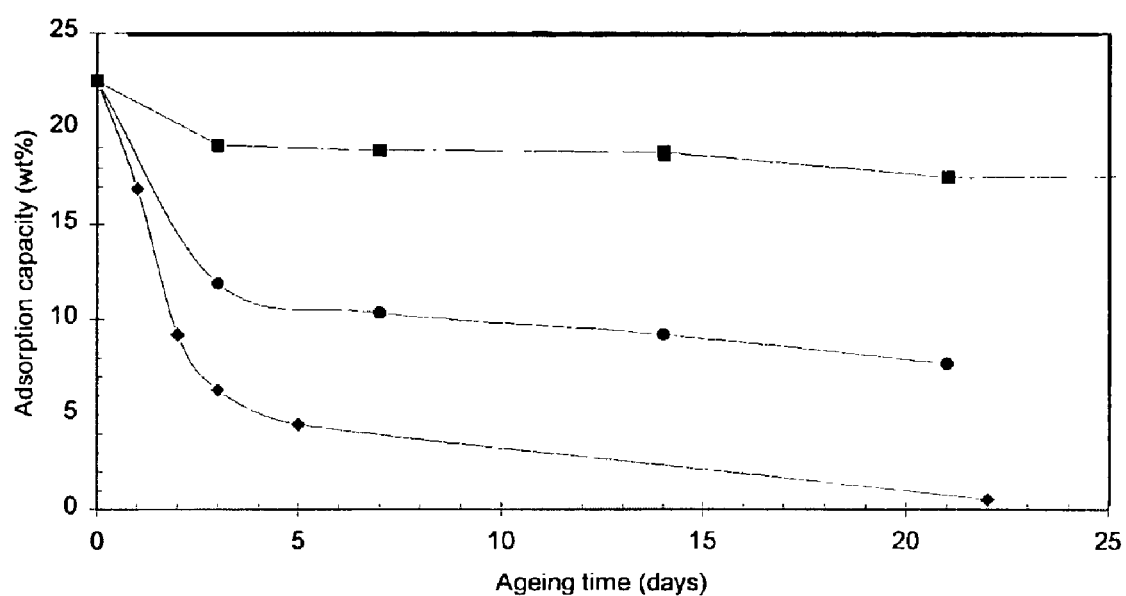
FIG. 2 shows the methanol adsorption capacity of a SAPO-34 molecular sieve after different $NH_3$-treatments as a function of the ageing time.

FIG. 2 shows the methanol adsorption capacity of SAPO-34 after different $NH_3$-treatments as a function of the ageing time (♦parent SAPO-34; ● SAPO-34 treated with $NH_3$ at 20° C. prior to the ageing treatment; ▲SAPO-34 treated with $NH_3$ at 150° C. prior to the ageing treatment; and ■SAPO-34 treated with $NH_3$ at 210° C. prior to the ageing treatment).

The methanol adsorption capacity is given as weight percent; this is the increase in weight percent of the calcined SAPO-34 after methanol uptake. This data clearly shows that the untreated SAPO-34 looses its methanol adsorption capacity rapidly with ageing. The ammonia chemisorption treatment at 20° C. shows a significant improvement in methanol adsorption capacity on ageing. The 150° C. and 210° C. treated samples show a marked improvement with maintenance of the SAPO-34 stability after extended periods of time.

Effect of Ageing on Methanol Conversion

Figure 3:
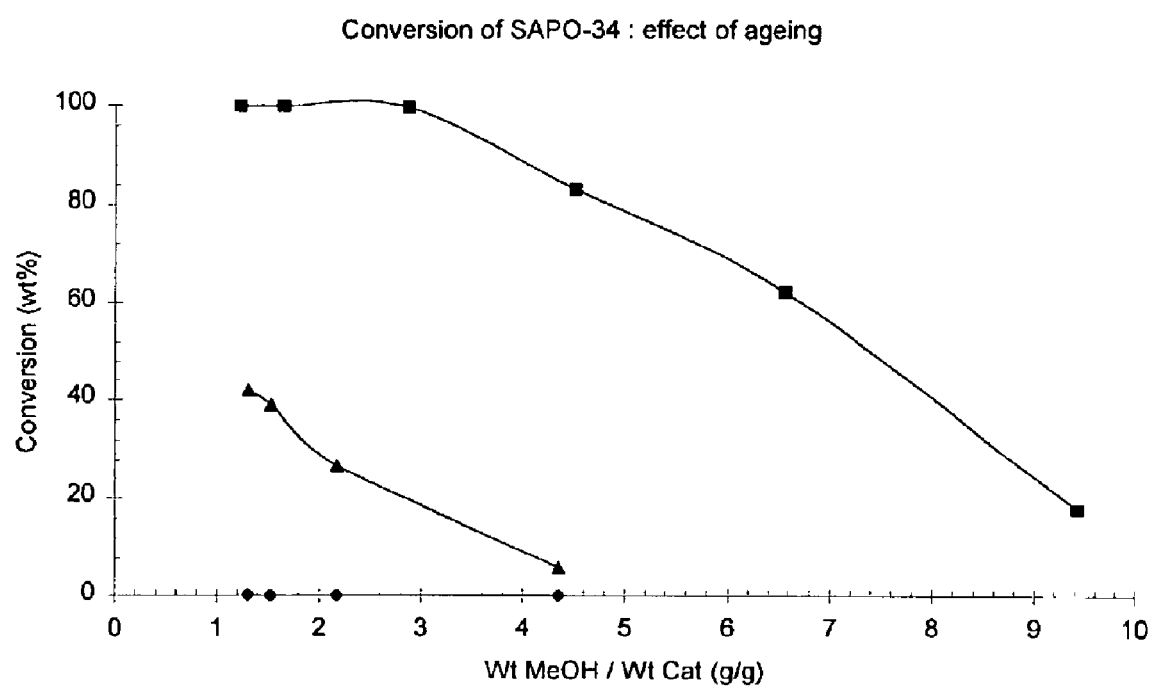
FIG. 3 shows the methanol conversion of a SAPO-34 molecular sieve after various periods of ageing.
Figure 4:
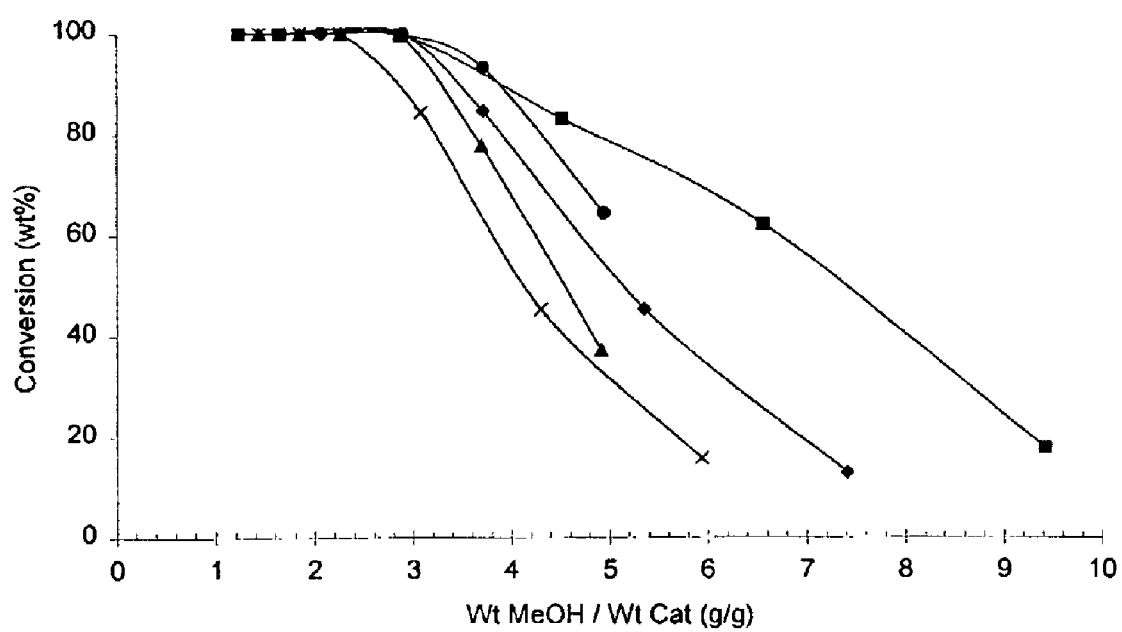
FIG. 4 shows the methanol conversion of an $NH_3$ treated SAPO-34 molecular sieve after various periods of ageing.

FIG. 3 shows the methanol conversion of SAPO-34 without ammonia chemisorption after various periods of ageing (■ parent SAPO-34, not aged; ▲ SAPO-34, aged for 3 days; ♦ SAPO-34, aged for 7 days). FIG. 4 shows the methanol conversion for ammonia chemisorbed SAPO-34 (treated at 210° C.) after various periods of extended ageing (■ parent SAPO34, not aged; ▲ SAPO-34, treated with $NH_3$, aged for 3 days; ♦ SAPO-34, treated with $NH_3$, aged for 6 days; ●SAPO-34, treated with $NI-I_3$, aged for 7 days; X SAPO-34, treated with $NH_3$, aged for 100 days).

FIG. 3 clearly shows how ageing has a detrimental effect on the MTO performance of a SAPO-34 catalyst, which looses all activity after only seven days ageing.

This is in contrast with the data shown in FIG. 4, which illustrates that even after extensive ageing (>100days) the $NH_3$, treated sample retains catalytic activity.

Pore Volume Data Calculated from $N_2$-Adsorption Isotherm

The pore volume data is provided in the following table.

| Sample | micropore volume (mL/g) |
|---|---|
| Parent SAPO-34, not aged | 0.249 |
| Parent SAPO-34, aged for 7 days | 0.006 |
| SAPO-34, treated with $NH_3$ at 210° C., aged for 7 days | 0.257 |
| SAPO-34, treated with $NH_3$ at 20° C., aged for 7 days | 0.111 |

This data illustrates that the $NH_3$ treatment has a positive effect on catalyst porosity on ageing. The treatment at 210° C. being particularly effective in maintaining porosity.

XRD Patterns of SAPO-34 Samples

Figure 5:
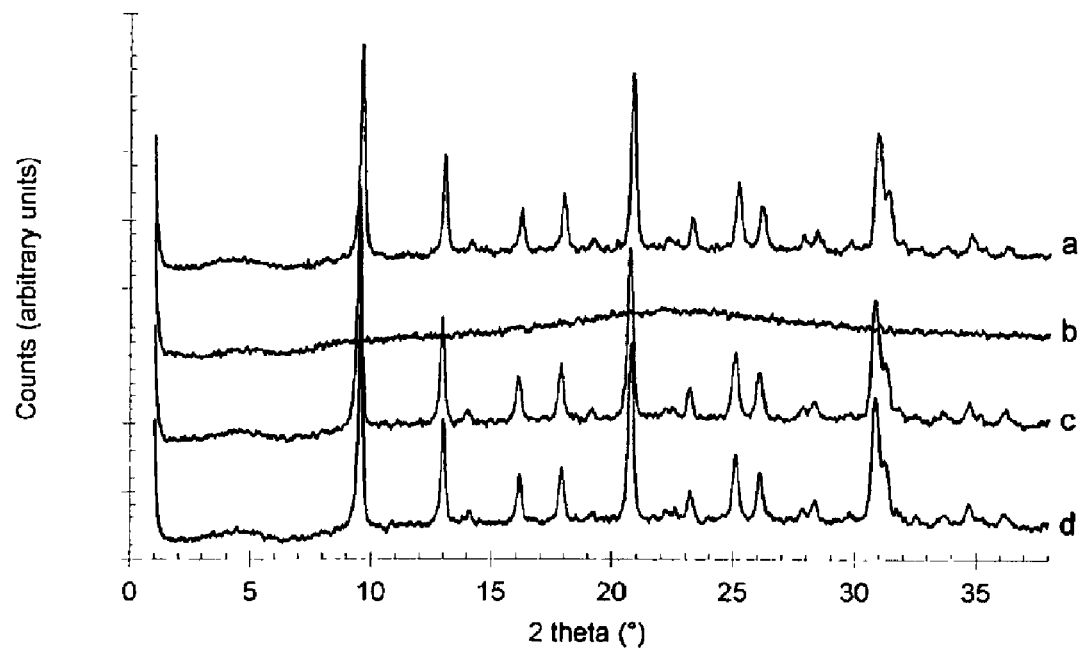
FIG. 5 shows the effect of ageing, with and without $NH_3$ treatment, on the XRD pattern of a SAPO-34 molecular sieve.

FIG. 5 illustrates the effect of ageing on the crystallinity of treated and untreated SAPO-34 catalysts (a=Parent SAPO-34, not aged, b=Parent SAPO-34, 22 days aged, c=SAPO-34, treated with $NH_3$ at 20° C., 22 days aged, and d=SAPO-34, treated with $NH_3$ at 210° C., 22 days aged). This figure shows that without the $NH_3$ treatment there is a complete loss of crystalline structure after only 22 days ageing. However, with $NH_3$ treatment the crystalline structure is retained on ageing.

IR Spectra

Figure 6:
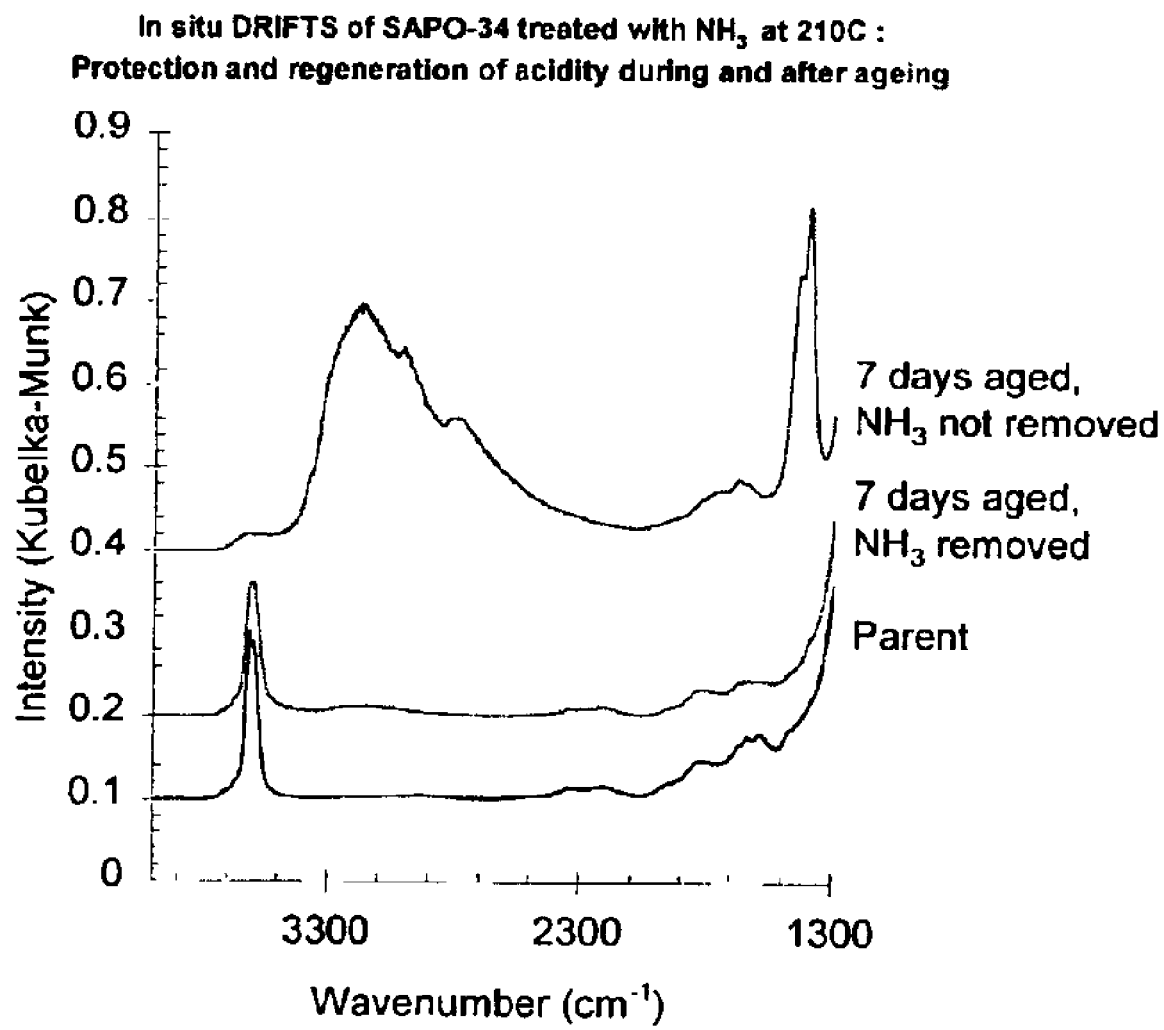
FIG. 6 shows DRIFTS Infrared spectra illustrating protection and regeneration of acidity during and after ageing of a SAPO-34 treated with $NH_3$.

FIG. 6 illustrates the effect of ammonia chemisorption and desorption on an activated SAPO-34 molecular sieve. The figure shows that after ammonia chemisorption the Broensted acid band at approximately 3650 $cm^{-1}$ is replaced by a series of new IR bands between 3500 $cm^{-1}$ and 2300 $cm^{-1}$. The figure also shows that these bands are retained during ageing of the ammonia chemisorbed molecular sieve and that after desorption of ammonia from the aged molecular sieve the original Broensted acid band returns indicating regeneration of the Broensted acid sites in the molecular sieve.

Example 3

Steam Ageing

SAPO-34 molecular sieves were prepared using the general procedure provided in Example 1. In addition samples were also prepared using a combined templating agent of dipropylamine (DPA) and tetraethylammonium hydroxide (TEAOH). The resultant SAPO-34 materials were activated by calcination to remove substantially all the organic template and were chemisorbed with ammonia at 210° C. using the method described above. These materials are referred to as SAPO-34 (M) for the morpholine templated material and SAPO-34 (D) for the dual templated material.

Ammonia chemisorbed samples and untreated samples of these SAPO-34 materials were exposed to steam in an SS Teflon lined autoclave, which was held at 110° C. under autogeneous pressure for up to 30 hours.

The samples before and after steaming were characterized using DRIFTS, XRD, methanol uptake and methanol conversion. The effectiveness of each sample in methanol conversion was also evaluated where appropriate after desorption of the chemisorbed ammonia, using the general procedure provided above.

SAPO-34 (M)

On steaming the untreated SAPO-34 showed almost complete loss of the Broensted acid infrared band after only 25 hours. However, the SAPO-34 (M) sample which had been treated with ammonia retained the Broensted acid infrared band after 25 hours of steaming; this band being regenerated after desorption of the chemisorbed ammonia.

The XRD demonstrated that under steaming the untreated parent SAPO-34 (M) experienced almost complete loss of crystallinity within 25 hours. This was contrasted with the SAPO-34 (M) samples treated with ammonia, which after ammonia desorption exhibited virtually no significant loss of crystallinity.

After steaming for 25 hours the untreated parent SAPO-34 (M) exhibited a methanol uptake index at 25 hours of only 0.11 whereas the ammonia chemisorbed SAPO-34 (M) sample exhibited a methanol uptake index of 0.89.

These results demonstrate that the SAPO-34 (M) samples with chemisorbed ammonia are remarkably resistant to hydrolytic attack by steam.

SAPO-34 (D)

The methanol conversion data for SAPO-34 (D) samples is provided in the following table:

| | | | Integrated Selectivities | | | |
|---|---|---|---|---|---|---|
| Sample | $CH_4$ | Ethylene | Ethane | Propylene | Propane | Total C4+ | Total Olefins |
| 1 | 0.84 | 32.12 | 0.81 | 41.43 | 2.58 | 22.22 | 73.56 |
| 2 | 1.25 | 28.85 | 0.80 | 38.89 | 6.13 | 24.08 | 67.75 |
| 3 | 1.10 | 31.84 | 0.93 | 40.40 | 4.37 | 21.36 | 72.22 |

Sample 1 = Untreated SAPO-34 (D) without steam ageing
Sample 2 = Untreated SAPO-34 (D) with steam ageing for 25 hours at 110° C.
Sample 3 = Ammonia chemisorbed SAPO-34 (D) with steam ageing for 25 hours at 110° C. and after desorption of chemisorbed ammonia.

This data illustrates that the steam ageing has a detrimental effect on the olefins yield when an untreated SAPO-34 (D) is used as MTO catalyst; in addition steaming also results in an increased production of propane which is undesirable. Although the ammonia chemisorbed SAPO-34 (D) does not have the same performance as the untreated fresh parent SAPO-34 (D) it does perform significantly better than the untreated aged sample. All of these SAPO-34 (D) samples showed virtually no loss of crystallinity on exposure to steam, which is in contrast to the effect of steam on the morpholine templated materials. In addition although the XRD data indicates that there is no significant loss of crystallinity for Sample 2 the methanol conversion data clearly demonstrates that this sample has lost a significant amount of catalytic activity on steam ageing.

While the present invention has been described and illustrated by reference to particular embodiments, those of ordinary skill in the art will appreciate that the invention lends itself to variations not necessarily illustrated herein. For example, it is also contemplated the molecular sieves described herein are useful as absorbents, adsorbents, gas separators, detergents, water purifiers, and other various uses such as agriculture and horticulture.

What is claimed is:

1. A method of providing a stabilized metalloaluminophosphate molecular sieve, which method comprises the steps of
   a. providing a metalloaluminophosphate molecular sieve having a framework structure,
   b. treating the metalloaluminophosphate molecular sieve with a source of ammonia under conditions to chemisorb ammonia with the metalloaluminophosphate molecular sieve, and
   c. maintaining the ammonia chemisorbed with the metalloaluminophosphate molecular sieve for a period of at least 24 hours.

2. The method of claim 1 wherein the metalloaluminophosphate provided in step a) comprises template within its framework structure.

3. The method of claim 2, wherein the template is removed from the framework structure of the molecular sieve prior to treatment of the molecular sieve with the source of ammonia.

4. The method of claim 3 wherein the entire template is removed prior to chemisorption of ammonia.

5. The method of claim 1 wherein ammonia is the source of ammonia.

6. The method of claim 5 wherein the ammonia is chemisorbed at a temperature within the range of 0 to 500° C.

7. The method of claim 3 wherein the ammonia is chemisorbed at a temperature within the range of 20 to 400° C.

8. The method of claim 1 wherein the ammonia is chemisorbed at a temperature greater than 100° C.

9. The method of claim 1 wherein the ammonia is chemisorbed at a temperature greater than 200° C.

10. The method of claim 3 wherein the ammonia is chemisorbed at a temperature greater than 100° C.

11. The method of claim 3 wherein the ammonia is chemisorbed at a temperature greater than 200° C.

12. The method of claim 1 wherein the molecular sieve is treated in the bulk state.

13. The method of claim 1, wherein the molecular sieve is selected from the group consisting of SAPO-18, SAPO-34, SAPO-35, SAPO 44, SAPO-47, MCM-2, metal containing forms of each of the foregoing, and mixtures thereof.

14. The method of claim 1, wherein the metalloaluminophosphate provided in step a) has been exposed to an oxygenate prior to treatment with the source of ammonia.

15. A method of providing an active metalloaluminophosphate molecular sieve, which method comprises the steps of
   a. providing a metalloaluminophosphate molecular sieve having a framework structure,
   b. treating the metalloaluminophosphate molecular sieve with a source of ammonia under conditions to chemisorb ammonia with the metalloaluminophosphate molecular sieve,
   c. maintaining the ammonia chemisorbed with the metalloaluminophosphate molecular sieve for a period of at least 24 hours, and
   d. desorbing the chemisorbed ammonia.

16. The method of claim 15 wherein the metalloaluminophosphate provided in step a) comprises template within its framework structure.

17. The method of claim 16, wherein the template is removed from the framework structure of the molecular sieve prior to treatment of the molecular sieve with the source of ammonia.

18. The method of claim 17 wherein the entire template is removed prior to chemisorption of ammonia.

19. The method of claim 15 wherein ammonia is the source of ammonia.

20. The method of claim 19 wherein ammonia is chemisorbed at a temperature within the range of 0 to 500° C.

21. The method of claim 18 wherein ammonia is chemisorbed at a temperature within the range of 20 to 400° C.

22. The method of claim 15 wherein ammonia is chemisorbed at a temperature greater than 100° C.

23. The method of claim 15 wherein ammonia is chemisorbed at a temperature greater than 200° C.

24. The method of claim 18 wherein the ammonia is chemisorbed at a temperature greater than 100° C.

25. The method of claim 18 wherein the ammonia is chemisorbed at a temperature greater than 200° C.

26. The method of claim 15 wherein the molecular sieve in treated in the bulk state.

27. The method of claim 15 wherein ammonia desorption is undertaken during manufacture of a catalyst composition.

28. The method of claim 15 wherein ammonia desorption is achieved by introduction of the ammonia chemisorbed molecular sieve into a conversion process.

29. The method of claim 28 wherein the conversion process is a methanol-to-olefins process.

30. The method of claim 15, wherein ammonia desorption takes place by heating the ammonia chemisorbed metalloaluminophosphate molecular sieve at a temperature in excess of 200° C.

31. The method of claim 30, wherein ammonia desorption takes place by heating the ammonia chemisorbed metalloaluminophosphate molecular sieve at a temperature in excess of 400° C.

32. The method of claim 31, wherein ammonia desorption takes place by heating the ammonia chemisorbed metalloaluminophosphate molecular sieve at a temperature in excess of 600° C.

33. The method of claim 15 wherein the molecular sieve is selected from the group consisting of SAPO-18, SAPO-34, SAPO-35, SAPO 44, SAPO-47, MCM-2, metal containing forms of each of the foregoing, and mixtures thereof.

34. The method of claim 15 wherein the metalloaluminophosphate molecular sieve provided in step a) has been exposed to an oxygenate prior to treatment with a source of ammonia.

35. A method for the manufacture of a catalyst composition, which method comprises the steps of
   a. forming a mixture comprising at least one metalloaluminophosphate molecular sieve having a framework structure with at least one binder material and/or at least another catalytically active material, and
   b. treating the mixture with a source of ammonia under conditions to chemisorb ammonia with the metalloaluminophosphate molecular sieve, wherein the ammonia in maintained chemisorbed with the molecular sieve for an extended period of at least two hours.

36. The method of claim 35 wherein the metalloaluminophosphate used in step a) comprises template within its framework structure.

37. The method of claim 36, wherein the template is removed from the microporous structure of the molecular sieve prior to treatment of the molecular sieve with the source of ammonia.

38. The method of claim 37 wherein the entire template is removed prior to chemisorption of ammonia.

39. The method of claim 35 wherein ammonia is the source of ammonia.

40. The method of claim 35 wherein ammonia is chemisorbed at a temperature within the range of 0 to 500° C.

41. The method of claim 38 wherein ammonia is chemisorbed at a temperature within the range of 20 to 400° C.

42. The method of claim 35 wherein ammonia is chemisorbed at a temperature greater than 100° C.

43. The method of claim 35 wherein ammonia is chemisorbed at a temperature greater than 200° C.

44. The method of claim 38 wherein ammonia is chemisorbed at a temperature greater than 100° C.

45. The method of claim 38 wherein ammonia is chemisorbed at a temperature greater than 200° C.

46. The method of claim 35 wherein the mixture is treated in the bulk state.

47. The method of claim 35 wherein the method further comprises the step c) of desorbing the chemisorbed ammonia from the metalloaluminophosphate molecular sieve.

48. The method of claim 47, wherein ammonia desorption takes place by heating the ammonia chemisorbed metalloaluminophosphate molecular sieve at a temperature in excess of 200° C.

49. The method of claim 48, wherein ammonia desorption takes place by heating the ammonia chemisorbed metalloaluminophosphate molecular sieve at a temperature in excess of 400° C.

50. The method of claim 49, wherein ammonia desorption takes place by heating the ammonia chemisorbed metalloaluminophosphate molecular sieve at a temperature in excess of 600° C.

51. The method of claim 35, wherein the metalloaluminophosphate molecular sieve used in step a) has been exposed to an oxygenate prior to ammonia chemisorption.

52. A method for the manufacture of a catalyst composition, which method comprises the steps of
   a. forming a mixture comprising at least one metalloaluminophosphate molecular sieve having ammonia chemisorbed thereon for an extended period of at least 2 hours, with at least one binder material and/or at least another catalytically active material, to form a catalyst composition.

53. The method of claim 52 further comprising the step of desorbing the ammonia after the catalyst composition has been formed.

54. A stabilized metalloaluminophosphate molecular sieve, which comprises at least one, aged metalloaluminophosphate molecular sieve and chemisorbed ammonia.

55. A method for storing metalloaluminophosphate molecular sieves which method comprises maintaining the metalloaluminophosphate molecular sieve in contact with ammonia in a chemisorbed state for a period of time of at least 24 hours during storage.

56. The method of claim 55 wherein the storage is for a period of at least 7 days.

57. The method of claim 56 wherein the storage is for a period of at least 30 days.

58. A method for protecting a metalloaluminophosphate molecular sieve from exposure to steam, which method comprises maintaining the metalloaluminophosphate molecular sieve in contact with ammonia in a chemisorbed state to stabilize catalytic activity while the metalloaluminophosphate molecular sieve is exposed to steam.

59. A stabilized molecular sieve composition comprising at least one metalloaluminophosphate molecular sieve in admixture with at least one binder and/or at least one other catalytically active material and chemisorbed ammonia sieve to maintain acid catalyst sites.

60. The stabilized molecular sieve composition of claim 59, wherein the molecular sieve is selected from the group consisting of SAPO-18, SAPO-34, SAPO-35, SAPO 44, SAPO47, MCM-2, metal containing forms of each of the foregoing, and mixtures thereof.

61. A stabilized molecular sieve composition comprising at least one metalloaluminophosphate molecular sieve having ammonia chemisorbed thereon, to maintain acid catalyst sites, and in admixture with at least one binder and/or at least one other catalytically active material.

62. A method for the manufacture of a stabilized catalyst composition, which method comprises the steps of
   a. forming a mixture comprising at least one metalloaluminophosphate molecular sieve having a framework structure with at least one binder material and/or at least another catalytically active material, and b. treating the mixture with a source of ammonia under conditions to chemisorb ammonia with the metalloaluminophosphate molecular sieve to maintain acid catalyst sites.

63. A method for the manufacture of a stabilized catalyst composition, which method comprises the steps of a. forming a mixture comprising at least one metalloaluminophosphate molecular sieve having ammonia chemisorbed thereon, to maintain add catalyst sites, with at least one binder material and/or at least another catalytically active material, to form a catalyst composition.

64. The stabilized molecular sieve composition of claim 61, wherein the molecular sieve is selected from the group consisting of SAPO-18, SAPO-34, SAPO-35, SAPO 44, SAPO-47, MCM-2, metal containing forms of each of the foregoing, and mixtures thereof.

* * * * *